United States Patent [19]

Palleja et al.

[11] Patent Number: 5,869,318
[45] Date of Patent: Feb. 9, 1999

[54] GENE SEQUENCE OF THE DOWN SYNDROME CRITICAL REGION OF HUMAN CHROMOSOME 21, IDENTIFIED BY A NEW "ALU-SPLICING PCR" TECHNIQUE, CODING FOR A PROLINE-RICH PROTEIN (DSCR1) HIGHLY EXPRESSED IN FOETAL BRAIN AND IN HEART AND METHOD FOR CHARACTERIZING IT

[75] Inventors: Xavier Estivill Palleja, Provenca 132, 08029 Barcelona, Spain; Juan Jose Fuentes; Melanie Pritchard, both of Barcelona, Spain

[73] Assignee: Xavier Estivill Palleja, Barcelona, Spain

[21] Appl. No.: 665,040

[22] Filed: Jun. 7, 1996

[30] Foreign Application Priority Data

Jun. 7, 1995 [ES] Spain .................................. P9501140

[51] Int. Cl.$^6$ ............................. C12N 1/20; C12N 15/63; C12N 15/85; C07H 21/04
[52] U.S. Cl. ................... 435/252.3; 536/23.5; 435/320.1; 435/325; 935/77; 935/78
[58] Field of Search ........................ 536/23.5; 435/320.1, 435/325, 252.3

[56] References Cited

PUBLICATIONS

Fuentes et al. Human Molecular Genetics (1995) vol. 4, No. 10, pp. 1935–1944.
Hassold, T.J. et la. "Trisomy in Man" Ann. Rev. Genet. 18, 69–97. (1984) pp. 69–95.
Lejeune, J. et al. "Etudes Chromosomiques . . . " C.R. Hebd. Spárces Acad. Sci. 248, 409–411 (1959).
Jacobs, P.A. et al. "The Somatic Chromosomes . . . " J. Lancet 1, 710–711 (1959).
Korenberg, J.R. et al. "Down Syndrome Phenotypes . . . " Proc. Natl. Acad. Sci. U.S.A. vol. 91, pp. 4997–5001, Genetics, May 1994.
McInnis, M.G. et al "A Linkage Map of Human . . . " Genomics 16, 562–571, 1993.
Bosch, A. et al. "The Eurogem Map . . . " Eur. J. Hum. Genet. 2, 244–245.
Chumakov, I. et al. "Continuum of Overlapping . . . " Nature, vol. 359, Oct. 1, 1992.
Nizetic, D. et al. "An Integrated YAC–Overlap . . . " Human Molecular Genetics, 1994, vol. 3, No. 5, 759–770.
Ichikawa, H. "A NotI Restriction Map . . . " Nature Genetics, vol. 4, Aug. 1993. pp. 361–366.
Cheng, J. F. "Isolation and Mapping . . . " Genomics 23, 75–84 (1984).
Kao, F.T. "Isolation and Refined Regional . . . " Genomics 23, 700–703 (1994).
Elvin, P. "Isolation of cDNA clones . . . " Nucleic Acids Research, vol. 18, No. 13, pp. 3913–3917.
Kao FT et al. "Chromosome Microdissection . . . " Proc. Natl. Acad. Sci. USA, vol. 88, pp. 1844–1848.
Duuk, G.M. "Exton trapping . . . " Proc. Natl. Acad. Sci. U.S.A. vol. 87, pp. 8995–8999 Nov. 1990.

(List continued on next page.)

*Primary Examiner*—Lisa B. Arthur
*Attorney, Agent, or Firm*—Ladas & Parry

[57] ABSTRACT

By means of a new molecular cloning technique designated "Alu-splicing PCR", we have isolated a new gene sequence, DSCR1, located in the 21q22.1-q22.2 region. DSCR1 displays a high expression in brain and heart, coding for a new protein with a proline-rich region and with some structural characteristics typical of a protein involved in transcription and/or in protein-protein interactions. The increase in the transient expression of DSCR1 mRNA in brains of young rats compared with the brains of adult rats suggests an important role of DSCR1 during the development of the central nervous system. The overexpression of pSCR1 may be involved in pathogenic abnormalities of mental retardation and/or heart defects in patients with Down syndrome.

8 Claims, 5 Drawing Sheets

OTHER PUBLICATIONS

Buckler, A.J. et al. "Exon amplification . . . " Proc. Natl. Acad. Sci. USA vol. 88 pp. 4005–4009, May 1991 Genetics.

M. Lovett et al. "Direct Selection: A Method . . . " Proc. Natl. Acad. Sci. U.S.A. vol. 88, pp. 9628–9632 Nov. 1991 Genetics.

S. Parimoo et al. "cDNA selection . . . " Proc. Natl. Acd. Sci. USA vol. 88, pp. 9623–9627 Nov. 1991, Genetics.

R. Wilson et al "2.2 M6 of Contiguous . . . " Nature vol. 368, Mar. 3, 1994, pp. 32–38.

Kozak, M. "At Least & Nucleotides . . . " J. Mol. Biol. (1987) 196 947–950).

Peterson, A. et al. "A Transcript Map . . . " Human Molecular Genetics, 1994, vol. 3, No. 10, 1735–1742.

McCormick, M.K. et al. "Molecular Genetic . . . " Genomics 5, 325–331 (1989).

Rahmani, Z. et al. "Critical Role of the D21SSS . . . " Proc. Natl. Acad. Sci. USA, vol. 86, pp. 5958–5962 Aug. 1989 Medical Science.

Korenberg, J.R. et al. "Down Syndrome . . . " Am. J. Hum. Genet. 50:294–302, (1992).

Landwchulz, W.H. et al. "the Leucine Zipper . . . " Science, vol. 240, pp. 1759–1764.

Murre, C. et al. "A New DNA Binding . . . " Cell, vol. 56, 777–783, Mar. 10, 1989.

Wolberger, C. et al. "Crystal Structure . . . " Cell, vol. 67, 517–528, Nov. 1, 1991.

Feng, S. et al. "Two Binding Orientations . . . " Science, vol. 266, Nov. 18, 1994.

H. Yu, et al, "Structural Basis . . . " Cell, vol. 76, 933–945, Mar. 11, 1994.

Koch, A.C. "SH2 and SH3 Domains: . . . " Science, vol. 252, pp. 668–674 (May 3, 1991).

Helin, K. et al. "Heterodimerization . . . " Genes & Development 7:1850–1861 (1993).

S. Hardy et al. "E2F from Adenovirus–Infected . . . " Moll. Cell. Biol. Oct. 1989 pp. 4495–4506, vol. 9, No. 10.

Fagan, R. et al. "Phosphorylation of E2F–1 . . . " Cell, vol. 78, 799–811, Sep. 9, 1994.

Pelech, S.L. et al. "Mirogen–activated protein . . . " TIBS 17, Jun. 1992 pp. 233–238.

Tijan, R. et al. "Transcriptional Activation . . . " Cell, vol. 77, pp. 5–8, Apr. 8, 1994.

Ptashne, M. "How Euraryotic Transcriptional . . . " Nature, vol. 335, Oct. 20, 1988; 683–689.

Songyong, Z et al, "SH2 Domains Recognize . . . " Cell, vol. 72, 767–778, Mar. 12, 1993.

Chumakov, I.M. et al. "Isolation of Chromosomes . . . " Nature, Genetics, vol. 1, Jun. 1992 222–225.

Tagle, D.A. et al. "An Optimized Alu–PCR . . . " Human Molecular Genetics, vol. 1, No. 2, pp. 121–122 (1992).

Sambrook, J. "Molecular Cloning" (Title Page Only) CSH—1989—Lab. Manual.

Raziuddin, A. "Receptors For Human . . . " Proc. Natl. Acad. Sci. USA pp. 5504–5508 (1984), vol. 81.

Gardiner, K. et al. "Partial Physical Map . . . " Somatic Cell & Molecular Genetics, vol. 14, No. 6, 1988 pp. 623–638.

Gardiner, K. et al. "Analysis of Human . . . " The EMBO Journal, vol. 9, No. 1, pp. 25–34 (1990).

Oberhausser, J. et al, "Encapsulation of Cells . . . " Focus a:3 8–9 (1987).

Adams, MD et al. "Rapid cDNA Sequencing . . . " Nature, Genetics, vol. 4, Aug. (1993), pp. 373–380.

Hill, C.S. Cell vol. 80, 199–211 Jan. 27, 1995.

```
                    A33
          GGTCGACCACCACTGCACTCCAGCCTGGGCGACAGAGCAAGACCCTGTCTCGA    50
          AGAAAAAAAAAAAAGTAATGACATCATCTAGTCAAGGGTCATATGCAGG         100
          TAAATTTCAACTCCTTTATTTTATTGTTATTTTCAG GCC AAA TTT          148
72H9-17.8                                        A   K   F        3
F54E7.7                                          -   N   F

72H9-17.8  GAG TCC CTC TTT AGG ACG TAT GAC AAG GAC ATC ACC TTT    188
            E   S   L   F   R   T   Y   D   K   D   I   T   F     16
F54E7.7     -   S   -   -   -   -   -   E   -   K   -   H   -

72H9-17.8  CAG TAT TTT AAG AGC TTC AAA CGA GTC AGA ATA AAC TTC    227
            Q   Y   F   K   S   F   K   R   V   R   I   N   E     29
F54E7.7     -   -   -   -   -   -   -   -   V   -   V   -   -

72H9-17.8  GAT TTT CCC TTC TCC GCA GAT GCC AGG CTC CAG CTG        266
            D   F   L   R   F   S   A   D   A   R   L   Q   L     42
F54E7.7     -   -   -   -   -   -   -   -   -   K   -   -   V

72H9-17.8  AGC AAC ACT GAG TTT CTG GGA AAG GAA ATG AAG TTA TAT    305
            S   N   T   E   F   L   G   K   E   M   K   L   Y     55
F54E7.7     -   S   -   -   -   -   -   -   -   -   -   -   -
                    5' sp1

72H9-17.8  CAT AAG ACT GAG TTT CTG GGA AAG GAA ATG AAG TTA TAT    328
            H   K   T   E   F   L   G   K   E   M   K   L   Y     58
F54E7.7     Q   -   -   -   -   -   -   -   -   -   -   -   -

72H9-17.8  TTT GCT CAG GTGAGTGCGGCCGC
            F   A   Q
F54E7.7     -   -   -
```

GENE SEQUENCE OF THE DOWN SYNDROME CRITICAL REGION OF HUMAN CHROMOSOME 21, IDENTIFIED BY A NEW "ALU-SPLICING PCR" TECHNIQUE, CODING FOR A PROLINE-RICH PROTEIN (DSCR1) HIGHLY EXPRESSED IN FOETAL BRAIN AND IN HEART AND METHOD FOR CHARACTERIZING IT

FIELD OF THE INVENTION

Down syndrome is one of the main causes of mental retardation and of congenital heart defects, which is predominantly the result of three copies of chromosome 21. Chromosome studies of rare patients with partial chromosome 21 trisomy have defined a minimum region for the Down syndrome phenotype which includes approximately 3 megabases (Mb) around the D21S55 marker. The overexpression of a new gene sequence, DSCR1 (SEQ ID NO:1), isolated from this region may be involved in pathogenic abnormalities of mental retardation and/or heart defects in patients with Down syndrome.

PRIOR ART

Down syndrome (DS) is the main cause of mental retardation and or congenital heart defects, which affects one in seven hundred newborn babies[1]. DS is associated with abnormalities in the gastrointestinal tract, an increase in the risk of contracting leukemia defects of the immune and endocrine systems, premature onset of Alzheimer's dementia and characteristic facial and physical features.

The relationship between DS and chromosome 21 trisomy was established 35 years ago[3,4]. Since then, a total of 43 new genes in chromosome 21 have been identified and cloned, but little progress has been made in our understanding of the disorder[5]. The presence of three copies of chromosome 21 should give rise to the overexpression of various genes, some of which would be responsible for several of the phenotypic features of DS. Although various genes may contribute to each specific abnormality observed in DS, it is possible to speculate that one gene alone may be responsible for each clinical characteristic. In fact, studies of cases with partial chromosome 21 trisomy suggest that particular regions of the chromosome contain the genes responsible for specific features of DS[6]. Although a minimum region has been proposed for the DS phenotype around the D21S55 marker, other studies suggest that genes located outside the D21S55 region contribute significantly to the main phenotype of DS[7,8]. Elucidation of the contribution of each of the individual genes to the main phenotypic features will be possible only through the isolation of each gene and the analysis of its expression and function. Of the whole of chromosome 21, the q22 region is the main target in the search for genes potentially involved in DS.

The characterization of chromosome 21 has advanced considerably over the last five years. With the development of new markers, the genetic map of this chromosome has achieved a resolution of better than 3 centimorgans (cM)[9,10]. Two physical maps of this chromosome have been obtained using overlapping YACS (yeast artificial ;chromosomes) and cosmid clones ordered along the long arm of the chromosome[11,12], and a complete NotI restriction map has been generated with its corresponding binding clones[13]. Recently, expression maps of chromosome 21 have been started, which will assist in identifying all the genes of this chromosome[14,15].

Various methods have been developed for the identification of coding sequences of specific regions of the genomic DNA. These methods include the hybridization of cDNAs on filters using genomic DNA as probe[16,17], the trapping[18,19], and the direct selection of cDNA clones (cDNA selection)[20,21].

The identification of genes of chromosome 21 is crucial for understanding the mechanisms involved in the various phenotypic manifestations of DS. Transcription maps of chromosome 21 and of the DS critical region have been developed, and work is continuing on obtaining them[14,15,24]. This effort will provide a catalogue of coding genes for this chromosome, which will enable us to study diseases linked to human chromosome 21. A region critical for DS (about 3 Mb around D21S55) covers the majority of the clinical features of DS, including mental retardation[7,25–27]. Another study has demonstrated that DS is a syndrome of contiguous genes and that the genes outside D21S55 also contribute to the DS phenotype[8]. Although these studies are based on a very small number of patients, the region around D21S55 is the main target for the identification of genes which are probably involved in DS. In this connection, a large number of patients have employed the presence of some polypeptide linked to genes present on chromosome 21 as instruments for diagnosis of the disease, especially in the gestation period. An example of these methods is that relating to the precursor protein of the amyloid β-peptide (EP 576,152). Similarly, probes specific for chromosome 21 employing Alu sequences (TC65 and 517) as specific initiators (FR 2,690,460) or complex cosmids which map in the 21q22 zone (WO93/18184) are described in the literature.

The screening of a gene library of cDNA from foetal brain ($1 \times 10^6$ lfu (lysis-forming units)) gave several positives. The DSCR1 protein deduced from the clones BC-17.8-1 and BC-17.8-2 has a 41% identity with the protein product deduced from F54E7.7 of C. elegans. The main difference between the two amino acid sequences lies in their length, since C. elegans protein has 20 amino acids more at the carboxy-terminal end and possesses 45 additional amino acids at the amino-terminal end. A search in the database for EST (expressed tagged sequences) showed that the human sequences 21ES87, 21ES127 and 21ES165 were almost identical to BC-17.8 in nucleotides 392 to 761, 724 to 1012 and 1200 to 1392, respectively, the last two corresponding to the untranslated 3' end of BC-17.8, and only 21ES87 contains part of the coding sequence[14]. Similarly, DSCR1 has a 65.4% identity at nucleotide level with the human brain EST EST07037 (T09144)[52].

Generally speaking, the homologies found between both nucleotide and polypeptide sequences, though high in some cases, correspond to only a part of the sequence described here, sometimes corresponding to very few residues and, except in the case mentioned above, not to coding residues. A search in the EMBL, Gen Bank, STRAND (European Patent Office) and SWISS PROT databases with respect to BC-17.8 reveals similarities only with deduced proteins of unknown function, F54E7.7 in chromosome III of C. elegans[22] and a protein of 24.1 kD (YKL159c) from the intergenic region PIR3-APE2 in chromosome XI of S. cerevisiae[30]. A more detailed analysis of smaller regions of the DSCR1 protein shows similarity with a large number of known proteins and peptides, identifying regions with some possible functional importance.

SUMMARY OF THE INVENTION

By means of a new molecular cloning technique designated "Alu-splicing PCR", we have isolated a new gene sequence, pSCR1 (SEQ ID NO:1), located in the 21q22.1–q22.2 region. DSCR1 (SEQ ID NO:1) displays a high expression in brain and heart, coding for a new protein with a proline-rich region and with some structural characteristics typical of a protein involved in transcription and/or in protein-protein interactions. The increase in the transient expression of DSCR1 (SEQ ID NO:1) mRNA in brains of young rats compared with the brains of adult rats suggests an important role of DSCR1 during the development of the central nervous system. The overexpression of DSCR1 (SEQ ID NO:1) may be involved in pathogenic abnormalities of mental retardation and/or heart defects in patients with Down syndrome.

BRIEF DESCRIPTION OF THE DRAWINGS

FIGS. 1A–1C show the identification of a putative exon of YAC 72H9 of chromosome 21.

FIGS. 2A–2C show the physical localization of the DSCR1 gene of human chromosome 21q22.

FIGS. 3A–3D show the analysis of expression of the DSCR1 gene.

FIGS. 4A–4C show the expression of DSCR1 mRNA.

DETAILED DESCRIPTION OF THE INVENTION

New Method for the identification of gene sequences

Figure 1A:
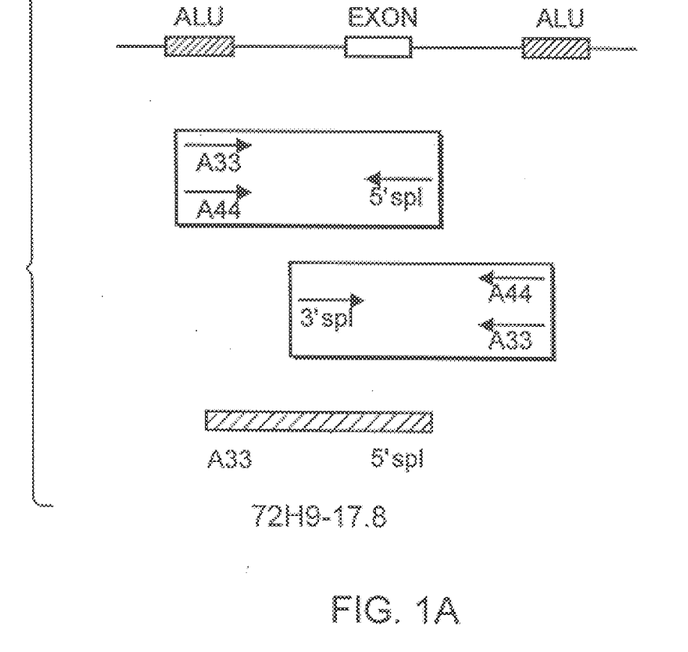
FIG. 1A is a diagrammatic representation of the cloning strategy by "Alu-splicing PCR" for the isolation of possible exons.

The method we describe here is based on the proximity of Alu repeat elements to one or more exons of a given gene. The system employs primers corresponding to the cutting and splicing (5'spl or 3'spl) acceptor and donor consensus sequences, in combinations with consensus primers for 5' or 3' sequences of Alu repeats. The sequences amplified using these combinations can include exons form any gene localized in the genomic sequence used as substrate for the amplification (FIG. 1a). This new method, designated "Alu-splicing PCR", has the limitation that not all exons are near to Alu repeats (A33 or A44) and that not all 5' or 3' splicing points are consensus, but the genes with a high number of exons will be readily identified by this method. Moreover, the Alu-splicing method has the advantage that mRNA (messenger RNA) or cDNA (complementary DNA) is not necessary for the detection of possible genes, and that whole YACs may be employed for the identification of exons. Since mRNA is not employed, the method does not depend on the levels of gene expression. Finally, as in the other methods, screening in cDNA libraries is needed in order to confirm the coding sequences and to obtain the complete length of the clones.

Figure 1B:
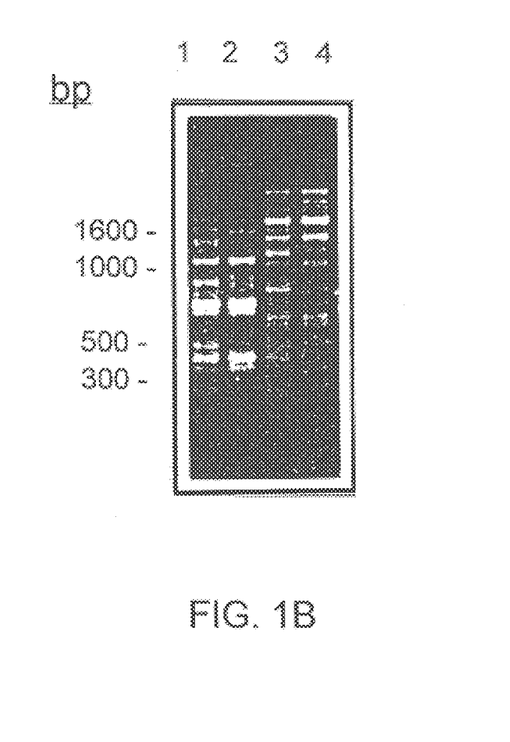
FIG. 1B shows PCR products stained with ethidium bromide and analyzed by electrophoresis on an agarose gel.

Among several possible exons of the q22.1–22.2 region identified by this technique, we have characterized one completely, which corresponds to the new gene sequence DSCR1 (SEQ ID NO:1). Amplifications using different combinations of 5'spl or 3' spl primers and A33 or A44 primers provide several fragments of the YACs 72H9 and 860G11. Since these YACs overlap on mpas of STSs (sequence tagged sites), the amplified products should also reflect this overlapping. FIG. 1b shows the common amplification of products detected between the two YACs using two combinations of primers. The subclones obtained from each of the four PCR reactions were sequenced, and possible homologies were sought in the public databases using the BLAST e-mail service at the NCBI. One of the clones, 72H9-17.8 (FIG. 1c), showed a 46% identity with the product deduced from the P54E7.7 gene of C. elegans[22]. Confirmation that the 72H9-17.8 sequence was obtained by means of a 5'spl-A33 amplification was carried out by means of hybridization with an internal oligonucleotide of the new sequence 72H9-17.8 on a filter which contained products of all the combinations of primers. YAC 860G11 was also positive for 72H9-17.8 (data not shown).

Identification of DSCR1 cDNA

The overlapping of two clones (BC-17.8-1 of 1.3 kb, and BC-17.8-2 of 2.0 kb) resulted in a cDNA of 2174 bp (FIG. 2). The sequence has an open reading frame of 513 nucleotides and encodes 171 amino acids; a putative ATG initiation codon, with the consensus sequence of Kozak[23] at the nucleotide at position 49, in frame with a termination codon, localized 9 bp and 42 bp upstream. In this way, the untranslated 5' region is 48 bp in length. The untranslated 3' region of DSCR1 is 163 bp. Two consensus polyadenylation signals were detected within the untranslated 3' region. The new gene sequence was designated Down syndrome critical region 1 (DSCR1) (SEQ ID NO:1).

DSCR1 is localized on human chromosome 21q22.1–q22.2

Figure 3A:
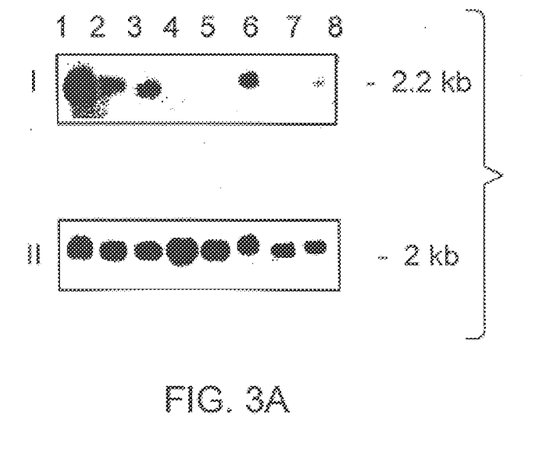
FIG. 3A is a northern analysis of adult mRNA.

The localization of DSCR1 (SEQ ID NO:1) on human chromosome 21 was confirmed by PCR with the cell line WAV17, which contains only human chromosome 21 in mouse cells. Subchromosomal localization using a panel of somatic hybrids showed that all the lines except 1x18 and 8q$^{-a}$ were positive for the new gene sequence, defining the localization of the latter in 21q22.1–22.2 (FIG. 3a).

Figure 3B:
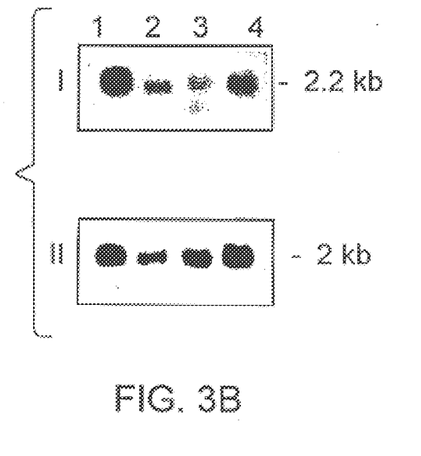
FIG. 3B is a northern analysis of fetal mRNA.
Figure 3C:
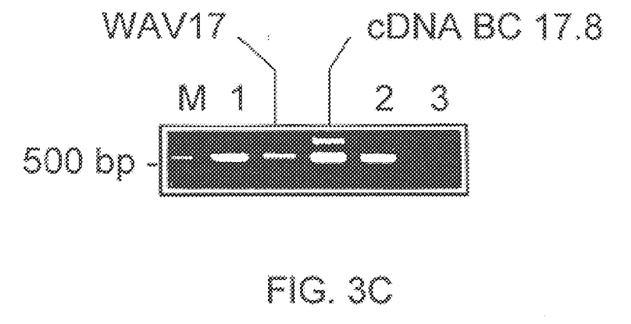
FIG. 3C shows the detection by RT-PCR of the DSCR1 mRNA in human lymphocytes.
Figure 3D:
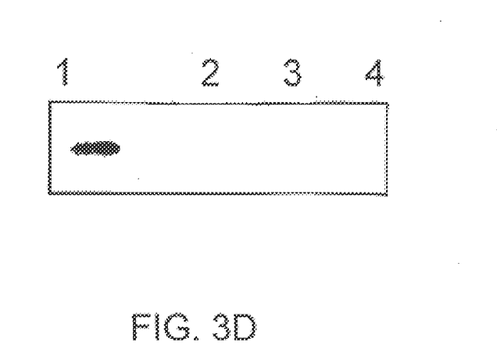
FIG. 3D is a northern analysis of total mRNA originating human brain and rat brain, heart and kidney.

A finger localization of 72H9-17.8 was carried out using YACs located in the subregion 21q22.1–q22.2 as templates for amplification with PCR. The following YACs were positive: 73D10, 72H9, 812F11, 860G11 and 916H12; while 520C10, 529C8, A222A12, 972C3, 212A5 and 230E8 were negative (FIG. 3b). Analysis of the cell lines of somatic hybrids with STSs of this region showed that 21q$^+$ (21pter→21q22) and 8q$^{-a}$ (21q→22gter) were both positive for AML1 and D21S65, but only 21q$^+$ contained the sequence of 72H9-17.8. A restriction map for PPGE (pulsed-field gel electrophoresis) was carried out using BC-17.8 as probe and the PCR products derived from markers present in the YACs 72H9 and 73D10, localizing gene sequence DSCR1 at approximately 400 kb from the locus of AML1 in the centromers direction (FIG. 3c).

Analysis of the expression of the gene sequence DSCR1

Figure 4A:
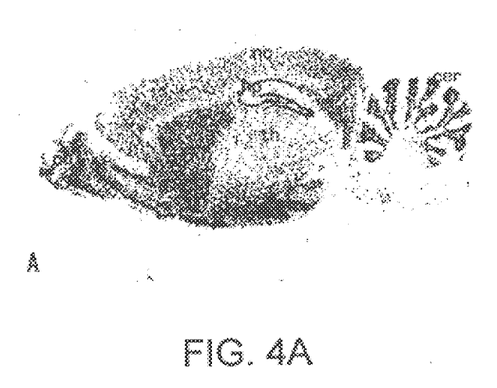
FIG. 4A is expression in adult rat brain.
Figure 4B:
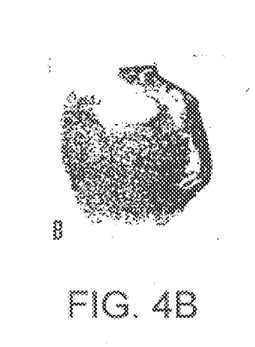
FIG. 4B is expression in adult rat heart and FIG. 4C is expression in adult rat liver.
Figure 4C:
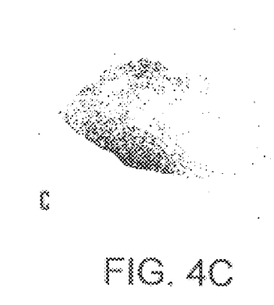

The analysis of expression of DSCR1 (SEQ ID NO:1) in human tissues by means of the Northern transfer method identified a transcript of about 2.2 kb. The highest levels of expression were detected in foetal brain and adult heart. Lower levels of expression were detected in adult brain, lung, liver, skeletal muscle, kidney and pancreas, and in the foetal period in lung, liver, kidney and placenta. A second transcript of 2.0 kb was detected in foetal and adult liver (FIGS. 4a and b). Levels of DSCR1 mRNA in peripheral blood lymphocytes, in fibroblasts of the cell line WAV17 and in brain were determined by RT-PCR (reverse transcription-PCR). Amplification was observed in lymphocytes and fibroblasts after carrying out two PCRs, the second with internal primers (nested PCR), but only one PCR amplification was needed in brain (FIG. 4c). A Northern transfer was also carried out with samples of rat brain, heart and kidney using BC-17.8 as probe, and the pattern of expression was similar to that for human tissue, also with more expression in brain and heart (FIG. 4d).

In situ hybridization studies were carried out in rats with a 40-bp antisense oligonucleotide derived form the DSCR1 human transcript. DSCR1 mRNA is expressed in adult and newborn rat tissues. In adult rats, the in situ hybridization signal was larger in particular regions of the brain and heart than in the liver (FIG. 4). The in situ hybridization signals form heart and from liver showed a fairly homogeneous distribution pattern, but hybridization signals with different intensities were found in some regions of adult brain, such as the neocortex, striate bodies, hippocampal formation, hypothalamus, thalamus, olfactory bulb and cerebellar cortex, and no signal at all was detected in the white matter. The largest in situ hybridization signal was localized in the olfactory bulb, piriform cortex pyramidal cell layer of the hippocampus, striate bodies and cerebellar cortex. Similarly, rats on days 2, 7 and 16 after birth expressed DSCR1 mRNA, although the signal in the neocortex and hypothalamus was larger in young rats than in adult rats. Comparatively, the largest in situ hybridization signal was detected on days P2 and P7, and decreased in the majority of the regions of the brain from day P16.

DSCR1 is a new gene sequence of chromosome 21

We describe here the isolation, characterization and analysis of expression of a new gene sequence (DSCR1) (SEQ ID NO:1) of the q22.1–22.2 region of human chromosome 21.

The new gene sequence DSCR1 has been localized by somatic hybrids, PFGE and maps of YACs in 21q22.1–22.2, at 400 kb from AML1, around 2 Mb of the D21S55 locus. Thus, DSCR1 is in a region considered to contribute significantly to the main phenotype of DS. The pattern of expression of DSCR1 mRNA and its distribution in tissues is consistent with the view that this gene is important in brain and heart, and consequently its overexpression in these tissues may cause some of the phenotypic features of DS. The absence of DSCR1 mRNA in the white matter of the central nervous system is compatible with neuronal expression. Nevertheless, this pattern does not reflect the neuronal density, since regions such as the striatum, in which the neuronal density is not particularly high, show, comparatively, high levels of DSCR1 mRNA. Moreover, the level of expression is probably unrelated to cell size, since regions with a similar degree of cell size have different signal intensities[28]. This implies that some neuronal subpopulations show a larger degree of expression of DSCR1 than others. Transient increases in the expression of DSCR1 mRNA in brains of young rats in comparison with those of adults suggest an especially important role of DSCR1 during the development of the central nervous system. Consequently, it is possible that abnormalities in the development of the brain may be due to the overexpression of DSCR1. Finally, the distribution of DSCR1 mRNA does not conform to any pattern of the phylogenetic scale[29]. Thus, DSCR1 may have a critical function in particular states of development and in specific neuronal subpopulations, regions of the brain which express, comparatively, high levels of DSCR1 mRNA. The high levels of expression of DSCR1 in heart suggest that it is also important for the function and/or development of the heart. The determination of the importance of DSCR1 in brain and in heart and its involvement in DS is carried out by means of functional studies, as the use of mice without any copy of the homologue of this DSCR1 human gene sequence in mouse (knock-out) and of transgenic mice which overexpress the sequence.

Protein deduced from DSCR1 and its function

The deduced protein sequence (SEQ ID NO:2) provides some keys to the possible function of DSCR1. The amino-terminal region of DSCR1 is extremely rich in leucines and phenylalanines (25%), residues 17 to 56 could form an alpha-helix. Although this region cannot be considered to be a leucine-zipper domain, a helix-loop-helix motif or a homeo domain, this region has the hydrophobicity and the amphipathic motifs characteristic of these types of regions and could be involved in the binding of DNA and/or in multimerization[31–33].

There are two regions rich in proline residues at residues 69 to 88. 80% of these residues, including 6 prolines, are identical to the product deduced from the F54E7.7 gene of C. elegans. Similarly, a 68% identity was observed with the hypothetical protein of 24.1 kD of yeast. The first proline-rich sequence in DSCR1 (position 69 to 75, HLAPPNPDK) shows great similarity with ligands of both classes I and II of the SH3 domains. The consensus sequence of these SH3 domain ligands is XpαPpXP, where P represents a proline, p is generally a proline, α is a hydrophobic residue and X corresponds to an unconserved residue[34,35]. SH3 domains are conserved sequences present in various signal proteins and/or proteins of the cytoskeleton, some of which are involved in tyrosine kinase-dependent signal transduction[36]. If this proline-rich motif in DSCR1 is really an SH3 domain ligand, it should interact with proteins which contain SH3 domains.

The second proline-rich sequence is DSCR1 shows identity with a large number of proline-rich proteins, including some transcription factors. Clues to the possible function of the motif SPPASPP may be found in the cellular transcription factor E2F-1[37]. The phosphorylation of two serines in the motif SPPPSSPPSS of E2F-1 inhibits its interaction with the product of the retinoblastoma gene and stimulates the interaction with the E4 protein of adenovirus[38]. It would appear that the phosphylation of E2F-1 facilitates the protein-protein interactions which may be essential for the transcription of E2A and/or the expression of other target cellular genes of E2F[39]. In DSCR1, the serines at positions 82 and 86 are in each case followed by a proline, and may consequently be regulated by protein kinases.

Seven of the nine residues between positions 140 and 148 of DSCR1 correspond to glutamic acids. The sequences with capacity to activate transcription are frequently negatively charged and increase the capacity of basal transcription factors to initiate transcription. Various types of transcriptional activators have been identified, which may be acid, glutamine-rich or proline-rich domains[41]. Many proteins with various functions, including some transcription factors, have a glutamic acid-rich domain. The glutamic acid domain of DSCR1 could interact with other components of the transcriptional apparatus.

Another noteworthy feature of the carboxyl end of DSCR1 is a motif (PYTPI) which includes amino acids 163 to 168 which could bind to SH2 domains. This type of domain binds with different regions with phosphotyrosines (pTyr), with a specificity determined by the next three residues from the carboxyl end to the pTyr[43]. The domain of the hypothetical SH2 ligand of DSCR1 coincides with the consensus and is similar to other SH2 ligands described in other proteins. The signal transduction induced by the possible phosphorylation on the tyrosine of this domain could involve it in processes of dimerization and/or binding to DNA[44].

In summary, the invention consists in the isolation and characterization of a new gene sequence (pSCR1) localized on human chromosome 21, in the Down syndrome critical region, which codes for a proline-rich protein, with structural characteristics of protein involved in transcription and/or in protein-protein interactions. The said protein displays a high expression in brain and in heart. The larger expression of DSCR1 in brains of young rats suggests an important role in the development of the central nervous system. Four features of the protein deduced from DSCR1 lead us to the view that it is involved in transcription processes and/or in protein-protein interactions: possible domain of binding to DNA, multimerization domain, two potential domains of transcriptional activation (one acid and the other proline-rich) and putative ligand domains for SH2 and SH3. All these features are among the characteristics of transcription factors and transcription enhancers[41]. Thus, it is possible to speculate that the overexpression of a transcription factor in the central nervous system may have an effect on several genes, whose overexpression could be directly responsible for the abnormal development of the brain in DS.

Methodology Used in the Implementation of the Invention

Characterization and cloning by "Alu-splicing" PCR.

The putative exons of the YACs 72H9 and 860G11 were amplified by PCR by virtue of their proximity to human Alu sequences. The splicing site primers are: NotI-5'spl, 5'-CGCGCGGCCGCACWYACCW-3' (SEQ ID NO:3) (5'-splice); SacII-3'spl: 5'-CGCCCGCGGTCNCAGGT-3' (SEQ ID NO:4) (3'-splice), where W represents A or T, Y represents T or C, and N represents any nucleotide. The Alu primers are:

SalI-A33: 5'-CGCGTCGACCACTGCACTCCAGCCTGGGCG-3'(SEQ ID NO:5); and

SalI-A44: 5'-CGCGTCGACGGGATTAGGCGTGAGCCAC-3'(SEQ ID NO:6)[45,46].

The primers were designed with a restriction target to permit directional cloning of the amplified fragments. The final volume of the "Alu-splicing PC" reactions was 25 μl with the following components: 40 mM KCl, 8 mM Tris-HCl (pH 8.3), 2.7–3.3 mM $MgCl_2$, depending on the purity of the sample of YAC DNA, 0.01% gelatin, 0.15 mM each deoxynucleotide, 20 pmol of each primer and 300 ng of template DNA. The PCR conditions were 94° C. for 20 s, 55° C. for 40 s and 74° C. for 2 min, in a total of 30 cycles. After the amplification, the PCR products were purified with phenol/chloroform, precipitating the DNA with ethanol, the latter being digested with the appropriate restriction enzymes and the products being subcloned into the vector pBluescript SK+ (Stratagene). The positive clones selected were sequenced using T3 for the sequence of the exon (splice side) or with T7 for the Alu sequence (Alu side), using an ABI373A automatic DNA sequencer and DyeDeoxy Terminators (Applied Biosystems). The human origin and the localization of the clones were determined using a panel of human and rodent hybrid cells containing whole chromosome 21 or parts of this chromosome. A panel of clones of YACs, including 72H9 and 860G11 and other YACs from other regions of chromosome 21, was used to confirm the localization of the Alu-splice clones.

Screening and analysis of the cDNA.

A gene library of cDNA from foetal brain subcloned into λgt10 was acquired from Clontech (Palo Alto, Calif.) and was inoculated into 20 plates at an average density of $5\times10^4$ lysis-forming units (lfu) per plate. The phages from each plate were recovered by covering the plates with SM buffer (100 mM NaCl, 10 mM $MgSO_4$, 50 mM Tris-HCl, pH 7.5, 0.01% gelatin) and, 12 hours later, the buffer was recovered by aliquoting it. The aliquots from each sub-gene library were used in subsequent PCR experiments. Two pairs of primers were synthesized taking as template the sequences of putative exons, identified by the Alu-splicing technique, and were used in the screening of these sub-gene libraries of cDNA described above[47]. The primers corresponding to one of the putative exon sequences (17.8-1: 5'-AGGACGTATGACAAGGACATC-3'; (SEQ ID NO:7) corresponding to nucleotides 79–98), and (17.8-2: 5'-TGAGCAAAATATAACTTCATTTCCT-3', (SEQ ID NO:8) complementary to nucleotides 206–230) were used to screen the gene library of cDNA already described using as probe the 17.8-2 primer terminally labelled with T4 polynucleotide kinase[47]. The positive phages were purified and the inserts were subcloned into pBluescript SK+ at the EcoRI target. The clones which contained the desired inserts were sequenced as described above. The complete sequence of the cDNA was obtained by synthesizing new primers on the sequences already analysed (primer waling), and was analysed using the BLAST program of the National Center for Biological Information (NCBI) to look for possible homologies.

Somatic hybrid cells and genomic samples.

The localization of DSCR1 on chromosome 21 was confirmed using DNA of the human-mouse hybrid cell line WAV17, which contains chromosome 21 as the only human chromosome[48]. The sublocalization of the clone 72H9-17.8 was determined by amplifying the DNA of the panel of the somatic hybrid cell line specific for human chromosome 21×Chinese hamster, composed of the following cell lines: 153E7b, 2Fur-1, ACEM, JC6, 6;21, 4;21, 1;21, 3;21, 10;21, 21;22, R2-10W, 7;21, 6918-8a1, 1x18C9, 3x2S, $8q^{-a}$, $21q^+$ and $MRC2G^{49,50}$. DNA from whole peripheral human blood, Chinese hamster DNA and mouse DNA were included as controls in the PCR experiments. DNAs of the cell lines were obtained from D. Patterson. The human DNAs were obtained from precipitates of lymphocytes by lysis with SDS, digestion with proteinase K and salt precipitation. The genomic cDNA probes were labelled with [$\alpha$-$^{32}$P]dCTP by "random priming".

YACs of human chromosome 21 and STSs.

The following YACs of human chromosome 21 were used in this study: 72H9, 860G11, 73D10, 520D10, 529C8, 230E8, 212A5 and 812F11 supplied by CEPH/Généthon[11] and A222A12, 972C3 and 916H12 supplied by D. Patterson. The yeasts which contained the desired YACs were grown in AHC⁻ selective medium and were encapsulated in agarose beads using a modification of the method described by Overhauser and Radio[51]. Sequence specific to these YACs were amplified by the use of PCR with the primers which flank the respective STSs. To produce the restriction map, the agarose beads were digested overnight with restriction enzymes and electrophoresis was carried out on a 1% agarose gel in 0.5× TBE. The DNA was transferred to Hybond N+ membranes in 0.4N NaOH. Hybridizations were carried out in 7% SDS/0.5M $NaP_2O_4$ buffer using probes labelled by "random priming".

The STSs which were analyzed are: D21S332, D21S328, D21S65, AML1, D21S393, D21S211 and D21S17. The primer pairs corresponding to the 5' and 3' sequence of DSCR1 were also used for its localization on the YACs and in the panels of somatic hybrids. PCR amplifications were carried out with 10 pmol of each primer, 1 mM $MgCl_2$ 40 mM KCl, 8 mM Tris-HCl (pH 8.3), 150 mM each dNTP, 100 ng of yeast DNA containing the relevant YAC and 0.5 units of Taq DNA polymerase (Boehringer Mannheim) in a final volume of 25 µl, using a Perkin-Elmer 9600 thermocycler. The initial denaturation time was 92° C. for 5 min, amplification proceeded for 30 cycles of 94° C. for 20 s, hybridization at 58° C. for 40 s and extension of 74° C. for 1 min.

RNA analysis.

Two northern blots (Clontech, Pal Alto, Calif.) containing poly(A)+ messenger RNA (mRNA) form adult and foetal human tissues were hybridized with probes labelled according to the protocol from the commercial firms. In addition, total RNA was isolated from lymphocytes and from brain, and poly(A)+ mRNA was prepared from rat brain, liver, heart, kidney and lung using the guanidine isothiocyanate method and the FastTract system (Invitrogen). Samples of human total RNA were also analyzed using reverse-transcription PCR (RT-PCR), employing 1 µg of total RNA and the GeneAmp RNA-PCR kit (Perkin Elmer).

In situ hybridizations of tissues.

Studies of in situ hybridizations in rat brain and in heart and oliver were carried out with an antisense synthetic oligonucleotide of 40 bases (5'-CAAAGG-TGATGTCCTTGTCATACGTCCTAAAGAGGGACTC-3') (SEQ ID NO:9) which is complementary to bases 136 to 97 of the human cDNA sequence of DSCR1. Adult rats and 2-, 7- and 16-day-old rats (3 rats per age studied) were sacrificed by decapitation, their tissues were rapidly extracted and frozen in dry ice, and 20 mm sections were cut with a cryostat at −20° C. and were kept at −20° C. coated with gelatin until required for use. The oligonucleotides were labelled with [$\alpha$-$^{32}$P]dATP (>3,000 Ci/mmol, NEN) with a specific activity of 1–10 µCi/pmol. Two pmol of each oligonucleotide were added to (50 µCi (5 ml) of [$\alpha$-$^{32}$P] dATP in the presence of 10 µl of cutting buffer (which contained 500 mM Na cacodylate pH 7.2, 10 mM $CoCl_2$ and 1 mM dithiotreitol) and 50 units of deoxynucleotidile terminal transferase (Boehringer Mannheim) and the mixture was incubated at 37° C. for 2 h. The labelled probe was purified using an ion exchange column (Pharmacia). The brain sections were dried and were fixed with 4% paraformaldehyde (in 0.1M phosphate buffered saline), and were then treated with 12 units/ml of predigested pronase (Calbiochem), dehydrated and incubated overnight at 42° C. with a mixture containing 40% deionized formamide, 0.6M NaCl, 1× Denhardt's solution (1× contains 0.02% Ficoll, 0.02% polyvinylpyrrolidone and 0.02% bovine serum albumin), 10 mM Tris-HCl pH 7.5, 1 mM ethylenediaminetetraacetic acid, 0.5 mg/ml yeast transfer RNA (Gibco BRL), 10% dextran sulphate and 10% of labelled probe. After hybridization, the sections were washed twice in 1× SSC (150 mM sodium chloride and 15 mM sodium citrate, pH 7.0) at 52° C. for 1 h each time. Subsequent experiments were carried out with different stringencies in the post-hybridization washes (SSC concentrations within the range 2× to 0.1×). In these cases, the sections were dehydrated in 70% and subsequently 95% ethanol., both solutions containing 0.3M ammonium acetate pH 7 for 5 min in each case, and then dried in the air. βmax films (Amersham) were exposed to the labelled sections for 7 days at −80° C. The sections were then stained with cresyl violet. Specific controls were included in the hybridizations, such as the sense probe and competitive experiments entailing addition of the non-radioactive antisense oligonucleotide (50 times the concentration of the antisense oligonucleotide) in the hybridization solution.

Application in transgenic animals

The gene homologous to DSCR1 in the mouse, Dscr1, has been identified from gene libraries of cDNA from several tissues (liver, brain and embryo). Transgenic mice are being developed which will enable the role of the DSCR1 gene in Down syndrome to be studied. A first transgenic animal would be that which expresses the DSCR1 gene under the control of the promoter of the PDGF-B gene, which directs the expression of the gene functioning effectively and specifically in the brain. The transgenic mice will be obtained by means of the micro-injection of the transgene into B6SJL×B6SJL embryos, and the presence of the chimeric gene will be identified by means of PCR and Southern Blotting. Positive animals are analysed from the standpoint of expression, localization and function of the DSCR1 protein. A second transgenic animal will be that which is obtained by means of the use of the antisense sequence Dscr1, with the object of curbing the expression of this gene in the mouse. These experiments also include crosses with mice carrying an extra chromosome which includes the Dscr1 gene. Since these mice have phenotypic characteristics of Down syndrome, the reversion of some of the features in the mouse will enable an advance to be made in our knowledge about the function of Dscr1/DSCR1 and its role in Down syndrome.

BIBLIOGRAPHY

1. Hassold, T. & Jacobs, P. Trisomy in man. *Annu. Rev. Genet.* 18, 69–97 (1984).
2. Epstein, C. J. The consequences of chromosome imbalance: principles, mechanisms, and models. *Cambridge University Press*, New York (1986).
3. Lejeune, J., Gautier, M. & Turpin, R. Etudes chromosomiques somatiques de neuf enfants mongoliens [Somatic chromosomal studies of nine mongol children]. *C. R. Hebd. Séances Acad. Sci.* 248, 409–411 (1959).
4. Jacobs, P., Baikie, A., Court-Bourn, W. & Strong, J. *Lancet* i, 710–711 (1959).
5. Delabar, J. M. et al. Report of the fourth international workshop on human chromosome 21. *Genomics* 18, 735–745 (19–93).
6. Epstein, C. et al. Protocols to establish genotype-phenotype correlations in Down syndrome. *Am. J. Hum. Genet.* 49, 207–235 (1991).
7. Delabar, J. M. et al. Molecular mapping of twenty-four features of Down syndrome on chromosome 21. *Eur. J. Num. Genet.* 1, 114–124 (1993).
8. Korenberg, J. R. et al. Down syndrome phenotypes: the consequencers of chromosomal imbalance. Proc. Natl. Acad. Sci-USA 91, 4997–5001 (1994).
9. McInnis, M. G. et al. A linkage map of human chromosome 21:43 PCR markers at average intervals of 2.5 cM. *Genomics* 16, 562–571 (1993).
10. Bosch, A., Guimerà, J., Pereira de Souza, A. & Estivill, X. The EUROGEM map of human chromosome 21. *Eur. J. Hum. Genet.* 2, 244–245 (1994).
11. Chumakov, I. et al. Continuum of overlapping clones spanning the entire human chromosome 21q. *Nature* 359, 380–386 (1992).

12. Nizetic, D. et al. An integrated YAC-overlap end 'cosmidpocket' map of the human chromosome 21. *Hum. Molec. Genet.* 3, 759–770 (1994).
13. Ichikawa, H., Hoseda, F., Arai, Y., Shimizu, K., Ohira, M. & Ohki, M. A. NotI restriction map of the entire long arm of human chromosome 21. *Nature Genet.* 4, 361–366 (1993).
14. Cheng, J. F., Boyertchuk, V. & Zhu, Y. .Isolation and mapping of human chromosome 21 cDNA: progress in constructing in a chromosome 21 expression map. *Genomics* 23, 75–84 (1994).
15. Kao, F. T. et al. Isolation and refined regional mapping of expressed sequences from human chromosome 21. *Genomics* 23, 700–703 (1994).
16. Elvin, P. et al. Isolation of cDNA clones using yeast artificial chromosomes probes. *Nucleic Acids Res.* 18, 3910–3917 (1990).
17. Kao, F. T. & Yu, J. W. Chromosome microdissection and cloning in human genome and genetic disease analysis. *Proc. Natl. Acad. Sci. USA* 88, 1844–1848 (1991).
18. Ducky, G. M., Kim, S. W., Myers, R. M. & Cox, D. R. Exon trapping: a genetic screen to identify candidate transcribed sequences in cloned mammalian genomic DNA. *Proc. Natl. Acad. Sci. USA* 87, 8995–8999 (1990).
19. Buckler, A. J. et al. Exon amplification: A strategy to isolate mammalian genes based on RNA splicing. *Proc. Natl. Acad. Sci. USA* 88, 4005–4009 (1991).
20. Lovett, M., Kere, J. & Hinton, L. M. Direct selection: a method for the isolation of cDNA encoded by large genomic regions. *Proc. Natl. Acad. Sci. USA* 88, 9628–9632 (1991).
21. Parimoo, S., Patanjali, S. R., Shukla, H., Chaplin, D. D. & Weissman, S. M. cDNA selection: Efficient PCR approach for the selection of cDNAs encoded in large chromosomal DNA fragments. *Proc. Natl. Acad. Sci. USA* 88, 9623–9627 (1991).
22. Wilson, R. et al. 2.2 Mb of contiguous nucleotide sequence from chromosome III of *C. elegans. Nature* 368, 32–38 (1994).
23. Kozak, M. At least six nucleotides preceding the AUG initiator codon enhance translation in mammalian cells. *J. Mol. Biol.* 196, 947–950 (1987).
24. Peterson, Al, Patil, N., Robbins, C., Wang, L., Cox, D. R. & Myers, R. M. A Transcript map of the Down syndrome critical region on chromosome 21. *Hum. Mol. Genet.* 5, 1735–1742 (1994).
25. McCormick, M. K. et al. Molecular genetic approach to the characterization of the "Down syndrome region" of chromosome 21. *Genomics* 5, 325–331 (1989).
26. Rahmani, Z. et al. Critical role of the D21S55 region on chromosome 21 in the pathogenesis of Down syndrome. *Proc. Natl. Acad. Sci. USA* 86, 5958–5962 (1989).
27. Korenberg, J. R., Bradley, C. & Disteche, C. M. Down syndrome: Molecular mapping of the congenital heart disease and duodenal stenosis. *Am. J. Hum. Genet.* 50, 294–302 (1992).
28. Swanson, L. W. Structure of the rat brain. Elvesier. Amsterdam, London, New York, Yokyo (1992).
29. Ebbesson, S. O. E. Comparative neurology of the telencephalon. Plenum Press. London, New York (1980).
30. Vandendol, M., Bolle, P. A., Dion, C., Portetelle, D. and Hilger, F. Unpublished NCBI gi:Z28159.
31. Landschulz, W. H., Johnson, P. F. & McKnight, S. L. The leucine zipper: a hypothetical structure common to a new class of DNA binding proteins. *Science* 240, 1759–1764 (1988).
32. Murre, C., McCaw, P. S. & Baltimore, D. A new binding and dimerization motif in immunoglobulin enhancer binding, daughterless, MyoD, and myc proteins. *Cell* 56, 777–783 (1989).
33. Wolberger, C., Vershon, A. K., Leu, B., Johnson, A. D. & Pabo, C. O. Crystal structure of a MATa2 homeodomain-operator complex suggests a general model for homeodomain-DNA interactions. *Cell* 67, 517–528 (1991).
34. Feng, S., Cheng, J. K., Yu, H., Simon, J. A. & Schreiber, S. L. Two binding orientations for peptides to the Src SH3 domain: development of a general model for SH3-ligand interactions. *Science* 266, 1241–1247 (1994).
35. Yu, H., Chen, J. K., Feng, S., Dalgarmo, D. C., Brauer, A. W. & Schreiber, S. L. Structural basis for the binding of proline-rich peptides to SH3 domains. *Cell* 76, 933–945 (1994).
36. Koch, C. A. Anderson, D., Moran, M. F., Ellis, C. & Pawson, T. SH2 and SH3 domains: elements that control interactions of cytoplasmic signaling proteins. *Science* 252, 668–674 (1991).
37. Helin, K. et al. Heterodimerization of the transcription factors E2F-1 and DP-1 leads to cooperative transactivation. *Genes Dev.* 7, 1850–1861 (1993).
38. Hardy, S. & Shenk, T. EF2 from adenovirus-infected cells binds cooperatively to DNA containing two properly oriented and spaced recognition sites. *Mol. Cell. Biol.* 9, 4495–4506 (1989).
39. Fagan, R., Flint, K. J. & Jones, N. Phosphorylation of E2F-1 modulates its interaction with the retinoblastoma gene product and the adenoviral E4 19 kDa protein. *Cell* 78, 779–811 (1994).
40. Pelach, S. L. & Sangera, J. S. Mitogen-activated protein kinases: versatile transducers for cell signaling. *Trends Biochem. Sci.* 17, 233–238 (1992).
41. Tjian, M. & Maniatis, T. Transcriptional activation: a complex puzzle with few easy pieces. *Cell* 77, 5–8 (1994).
42. Ptashne, M. How eukaryotic transcriptional activators work. *Nature* 335, 683–689 9(1988).
43. Songyang, Z. et al. SH2 domains recognize specific phosphopeptide sequences *Cell* 72, 767–778 (1993).
44. Hill, C. S. & Treisman R. Trsanscriptional regulation by extracellular signals: mechanisms and specificity. *Cell* 80, 199–211 (1995).
45. Chumakov, I. et al. Isolation of chromosome 21-specific yeast artificial chromosome from a total human genome library. *Nature Genet.* 1, 222–225 (1992b).
46. Tagle, D. A. & Collins, F. S. An optimized Alu-PCR primer pair for human-specific amplification of YACs and somatic cell hybrids. *Hum. Molec. Genet.* 1, 121–122 (1992).
47. Sambrook, J., Fritsch, E. F. & Maniatis, T. *Molecular cloning: a laboratory manual.* 2nd edn (Cold Spring Harbor Laboratory Press, New York, 1989).
48. Raziuddin, A., Sarkar, F. H., Dutkowski, R., Shulman, L., Ruddle, F. H. & Gupta, S. L. Receptors for human alpha and beta interferon but not gamma interferon are specified on human chromosome 21. *Proc. Natn. Acad. Sci. USA* 81, 5504–5508 (1984).
49. Gardiner, K., Watkins, P., Munke, M., Drabkin, H., Jones, C. & Patterson, D. Partial physical map of human chromosome 21. *Somat. Cell. Molec. Genet.* 14, 623–638 (1988).
50. Gardiner, K. et al. Correlation of physical and cytogenetic maps: gene and CpG island distributions. *EMBO J.* 9, 25–34 (1990).
51. Overhausen, J. & Radic, M. Z. Encapsulation of cells in agarose beads for use with pulsed-field gel electrophoresis *Focus* 9, 8–9 (1987).

52. Adams, M. D. et al. Rapid cDNA sequencing (expressed sequence tags) from a directionally cloned human infant brain cDNA library. *Nature Genetics* 4, 373–389 (1993).

EXPLANATION OF THE FIGURES

FIG. 1

Figure 1C:
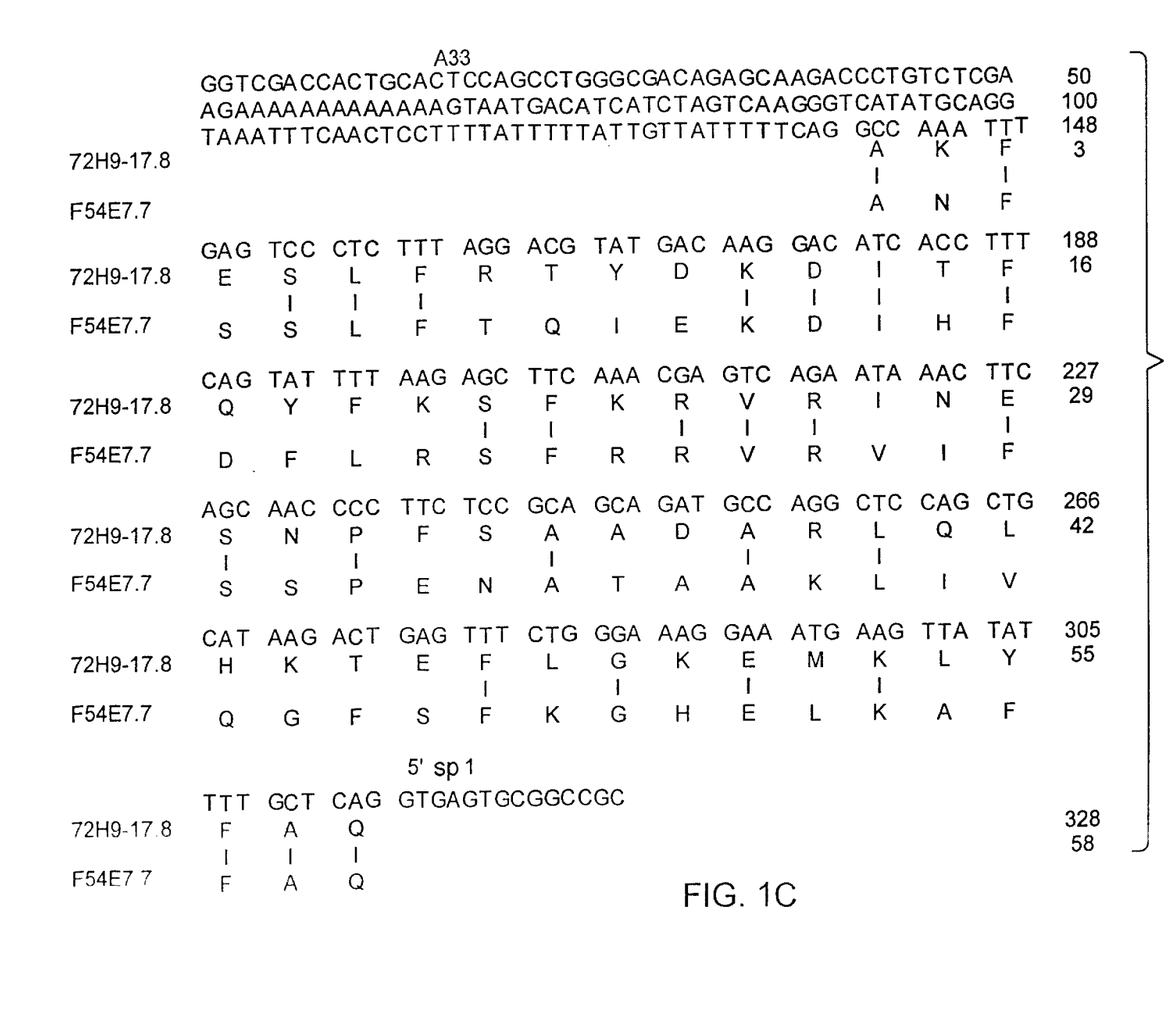
FIG. 1C is the DNA sequence of clone 72H9-17.8.

Identification of a putative exon of the YAC 72H9 of chromosome 21. A/ Diagrammatic representation of the cloning strategy by "Alu-splicing PCR" for the isolation of possible exons from a particular region of cloned DNA. A33 and A44 are primers derived form the consensus sequence of the Alu repeats, localized at the 3' and 5' ends, respectively. 3'spl and 5'spl are primers for consensus sequences involved in the cutting and splicing of exons. Combinations of Alu primers (A33 and A44) with splicing primers (3'spl and 5'spl) were employed. The clone described here was obtained with the combination of A33 and 5'spl. B/ PCR products stained with ethidium bromide and analysed by means of electrophoresis on a 2% agarose gel, obtained with the combinations of Alu and splicing primers employing the YACs 860G1 (lanes 1 and 3) and 72H9 (lanes 2 and 4) as template. C/ DNA sequence of the clone 72H9-17.8. The sequences which correspond to the primers used to generate this DNA fragment are shown in bold type; a putative 3' splicing sequence is shown in italics; the abovementioned amino acid sequence is written underneath each codon. Residues which are identical are indicated by a vertical line. The numbers at the right of the figure indicate the positions of the nucleotides and of the amino acids.

FIG. 2

Figure 2A:
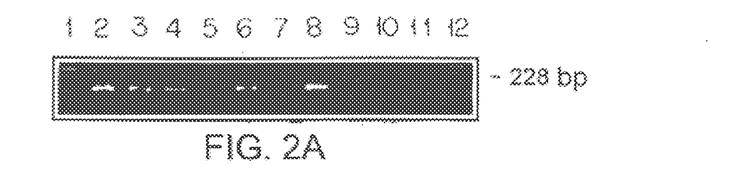
FIG. 2A shows the subchromosomal localization of 72H9-17.8 on 21q22.1–22.2 using hybrid cell lines.
Figure 2B:
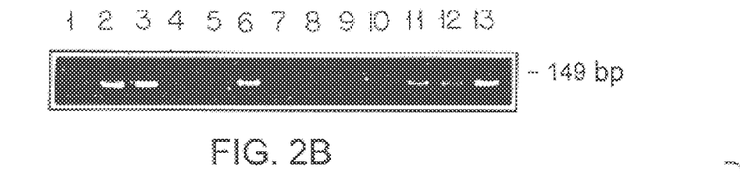
FIG. 2B shows the subregional localization of the DSCR1 gene sequence in the YACs originating from the 21q22.1–22.2 region.
Figure 2C:
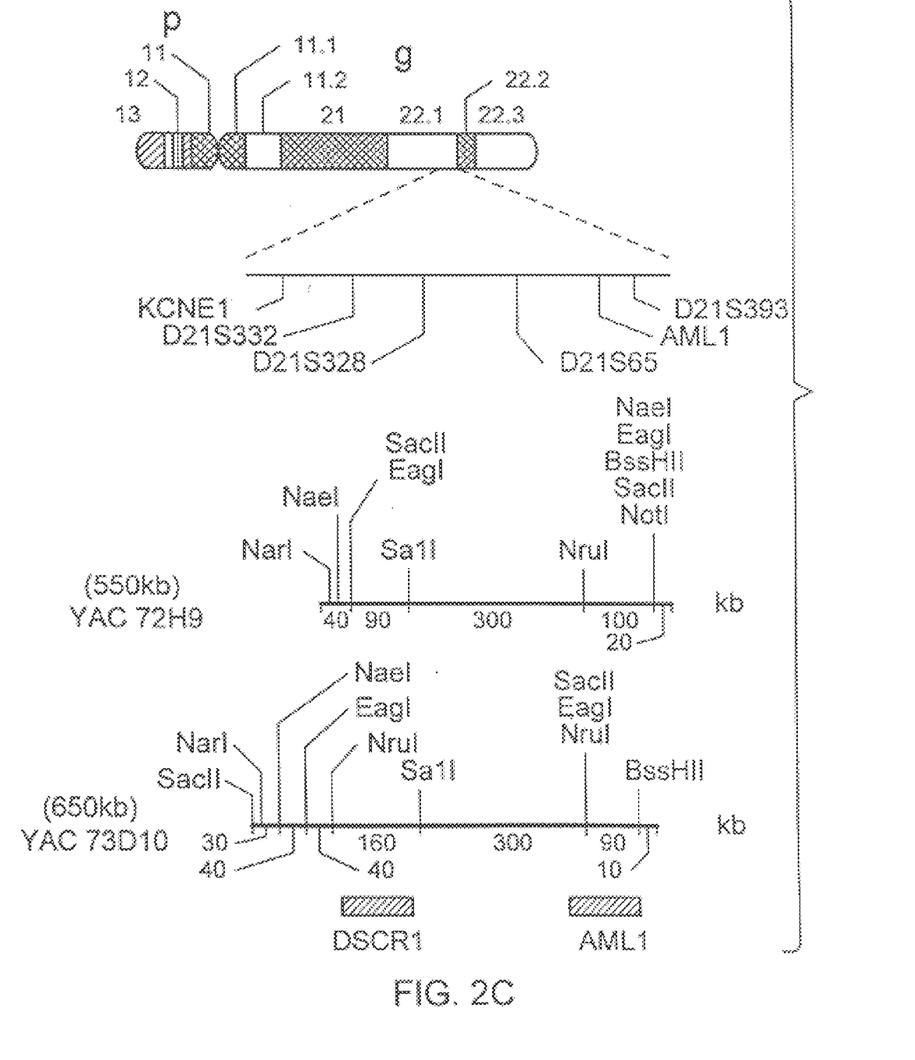
FIG. 2C is a diagrammatic representation of the 21q22.1–22.2 region.

Physical localization of the DSCR1 gene on human chromosome 21q22. A/ Subchromosomal localization of 72H9-17.8 on 21q22 using hybrid cell lines. PCR was carried out with the primers 17.8-Int. (intron) and 17.8-2 (exon). 1, 1-kb marker; 2, 3x2S; 3, 6918-8a1; 4, MRC2G; 5, 8q$^{-a}$; 6, 21q$^+$; 7, 1x18C9; 8, WAV17; 9, chinese hamster; 10, mouse; 11, water; 12, 1-kb marker. The size of the amplified product of 228 bp is indicated. B/ Subregional localization of the DSCR1 gene sequence in the YACs originating from the 21q22.1–22.2 region. PCR was carried out with the primers 17.8-1 and 17.8-2 (both for the exon sequence). 1, 1-kb marker; 2, 72H9; 3, 860G11; 4, 520C10; 5, A222A12; 6, 730D10; 7, 529C8; 8, 230E8; 9, 972C3; 10, 212A5; 11, 812F11; 12, 916H12 and 13, WAV17. The size of the amplified product of 149 bp is indicated. C/ Diagrammatic representation of the 21q22.1–22.2 region. Map of STS, overlapping of the YACs and restriction map of the clones of the YACs 72H9 and 73D10. The shaded rectangles correspond to the regions encoded by the DSCR1 and AML1 genes.

FIG. 3

Analysis of expression of the DSCR1 gene sequence. 2 mg of poly(A)+ RNA were hybridized with a cDNA BC-17.8 probe. A/ Northern analysis of adult mRNA. (I) DSCR1 (II) β-actin. The tissues tested were: (1) heart, (2) brain, (3) placenta, (4) lung, (5) liver, (6) skeletal muscle, (7) kidney and (8) pancreas. B/ Northern analysis of foetal mRNA. (I) DSCR1 and (II) β-actin. The tissues tested were: (1) brain, (2) lung, (3) liver and (4) kidney. C/ Detection by RT-PCR of the DSCR1 mRNA in human lymphocytes (1) and in brain (2); water blank (3). The primers used for the amplification were 17.8–1.1 (5'-TGGGAT-GGAAACAAGTGGAA-3') (SEQ ID NO:10) for nucleotides 314–333 and 17.8–1.4 (5'-GTTTTCT-CAAGACAGTCCCAA-3') (SEQ ID NO:11) complementary to nucleotides 813–833. The lymphocyte mRNA was previously amplified with the external primer pair 17.8-1 and 17.8-1.2 (5'-ATCAGTAATATACATGCACAAA-3') (SEQ ID NO:12) complementary to nucleotides 1089–1068. The long fragment detected on the amplification of the clone of cDNA BC-17.8 is an artefact. D/ Northern analysis of total mRNA originating from adult human brain (1) and poly(A)$^+$ RNA from rat brain (2), heat (3) and kidney (4).

FIG. 4

Expression of DSCR1 mRNA in adult rat brain (A), heart (B) and liver (C). The saggital section of the brain shows a strong signal in the olfactory bulb (ob) striate bodies (str) hippocampus (hp) and cerebellum (cer). No signal was observed in the white matter, th: thalamus, ne: neocortex.

---

We claim:

1. An isolated DNA sequence having the sequence identified as SEQ ID NO:1.

2. An expression vector comprising the DNA sequence of claim 1.

3. A host cell comprising the DNA sequence of claim 1.

4. An isolated DNA sequence having the sequence identified as SEQ ID NO:1, said sequence coding for a protein having the peptide sequence of SEQ ID NO:2.

5. An isolated DNA sequence having the sequence identified as SEQ ID NO:1 isolated by the process comprising amplifying, cloning and characterizing coding DNA sequences by employing an Alu-splicing PCR technique and using primers corresponding to the cutting and splicing 5'spl or 3'spl acceptor and donor consensus sequences, in combination with consensus primers for 5' or 3' sequences of Alu repeats.

6. The DNA sequence of claim 5 wherein the process for isolating the DNA sequence further comprises primers to amplify the restriction targets NotI, SacII and SalI, said primers having the sequences:

NotI-5' spl(5'-CGCGCGGCCGCACWYACCW-3'(5'-spl));

SacII-3' spl(5'-CGCCCGCGGTCNCAGGT-3'(3'-spl)), where W represents A or T, Y represents T or C, and N represents any nucleotide; and Alu primers:

SalI-A33(5'-CGCGTCGACCACTGCACTCCAGCCTGGGCG-3'); and

SalI-A44(5'-CCGTCGACGGGATTACAGGCGTGAGCCAC-3').

7. The DNA sequence of claim 5 isolated by a process that further comprises a digestion of the coding DNA sequences, amplified, cloned and characterized by employing an Alu-splicing PCR technique according to claim 5, with restriction enzymes and further subcloning into a vector.

8. The DNA sequence of claim 5 characterized by means of sequencing with a primer complementary to T3 exon and by means of a primer complementary to T7 sequences for an Alu-sequence.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 2174 base pairs
        ( B ) TYPE: nucleic acid
        ( C ) STRANDEDNESS: double
        ( D ) TOPOLOGY: circular     ( i i ) MOLECULE TYPE: cDNA for mRNA     ( i i i ) HYPOTHETICAL: No     ( i v ) ANTI-SENSE: No     ( v i ) ORIGINAL SOURCE: human
        ( A ) ORGANISM: Homo sapiens
        ( D ) DEVELOPMENTAL STAGE: foetal
        ( F ) TISSUE TYPE: Brain     ( v i i ) IMMEDIATE SOURCE: gene library of cDNA
        ( A ) LIBRARY: gene library of cDNA from foetal brain (B) CLONE: BC-17.8-1 and BC-17.8-2

(viii) POSITION IN GENOME:
    (A) CHROMOSOME/SEGMENT: chromosome 21/YAC 72H9
    (B) MAP POSITION: 21q22.1- q22.2

(ix) FEATURE:
    (A) NAME/KEY: cDNA for mRNA, BC- 17.8
    (B) LOCATION: 1..2174

(ix) FEATURE:
    (A) NAME/KEY: untranslated 5'
    (B) LOCATION: 1..48

(ix) FEATURE:
    (A) NAME/KEY: coding sequence
    (B) LOCATION: 49..560
    (D) OTHER INFORMATION: Down Syndrome critical region 1 (DSCR1)

(ix) FEATURE:
    (A) NAME/KEY: DSCR1
    (B) LOCATION: 1..171 PEPTIDES
    (C) IDENTIFICATION METHOD: translation of the DSCR1 sequence.
    (D) OTHER INFORMATION:
        - deduced protein
        - proline-rich protein domains
        - glutamic acid-rich protein domains
        - leucine/phenylalanine-rich protein domains (ix) FEATURE:
    (A) NAME/KEY: untranslated 3'
    (B) LOCATION: 564..2174

(ix) FEATURE:
    (A) NAME/KEY: 2 poly (A)
    (B) LOCATION: 1541..1546 AND 2132..2137

(xi) SEQUENCE DESCRIPTION: SEQ ID NO:1:

```
GAACTATAGT    TGAAGGCTGC    TGCCAATACA    ACACCACTGT    GAAACAGA                    48

ATG  GTG  TAT  GCC  AAA  TTT  GAG  TCC  CTC  TTT  AGG  ACG  TAT  GAC              90
Met  Val  Tyr  Ala  Lys  Phe  Glu  Ser  Leu  Phe  Arg  Thr  Tyr  Asp
 1              5                        10

AAG  GAC  ATC  ACC  TTT  CAG  TAT  TTT  AAG  AGC  TTC  AAA  CGA  GTC              132
Arg  Asp  Ile  Thr  Phe  Gln  Tyr  Phe  Lys  Ser  Phe  Lys  Arg  Val
 15                       20                       25

AGA  ATA  AAC  TTC  AGC  AAC  CCC  TTC  TCC  GCA  GCA  GAT  GCC  AGG              174
Arg  Ile  Asn  Phe  Ser  Asn  Pro  Phe  Ser  Ala  Ala  Asp  Ala  Arg
      30                       35                       40

CTC  CAG  CTG  CAT  AAG  ACT  GAG  TTT  CTG  GGA  AAG  GAA  ATG  AAG              216
Leu  Gln  Leu  His  Lys  Thr  Glu  Phe  Leu  Gly  Lys  Glu  Met  Lys
           45                       50                       55

TTA  TAT  TTT  GCT  CAG  ACC  TTA  CAC  ATA  GGA  AGC  TCA  CAC  CTG              258
Leu  Tyr  Phe  Ala  Gln  Thr  Leu  His  Ile  Gly  Ser  Ser  His  Leu
                60                       65                       70

GCT  CCG  CCA  AAT  CCA  GAC  AAG  CAG  TTT  CTG  ATC  TCC  CCT  CCC              300
Ala  Pro  Pro  Asn  Pro  Asp  Lys  Gln  Phe  Leu  Ile  Ser  Pro  Pro
                     75                       80

GCC  TCT  CCG  CCA  GTG  GGA  TGG  AAA  CAA  CTG  GAA  GAT  GCG  ACC              342
Ala  Ser  Pro  Pro  Val  Gly  Tyr  Lys  Gln  Val  Glu  Asp  Ala  Thr
 85                       90                       95

CCA  GTC  ATA  AAC  TAT  GAT  CTC  TTA  TAT  GCC  ATC  TCC  AAG  CTG              384
Pro  Val  Ile  Asn  Tyr  Asp  Leu  Leu  Tyr  Ala  Ile  Ser  Lys  Leu
     100                      105                      110

GGG  CCA  GGG  GAA  AAG  TAT  GAA  TTG  CAC  GCA  GCG  ACT  GAC  ACC              426
Gly  Pro  Gly  Glu  Lys  Tyr  Glu  Leu  His  Ala  Ala  Thr  Asp  Thr
          115                      120                      125

ACT  CCC  AGC  GTG  GTG  GTC  CAT  GTA  TGT  GAG  AGT  GAT  CAA  GAG              468
Thr  Pro  Ser  Val  Val  Val  His  Val  Cys  Glu  Ser  Asp  Gln  Glu
               130                      135                      140
```

-continued

```
AAG GAG GAA GAA GAG GAA ATG GAA AGA ATG AGG AGA CCT AAG        510
Lys Glu Glu Glu Glu Glu Met Glu Arg Met Arg Arg Pro Lys
            145                 150

CCA AAA ATT ATC CAG ACC AGG AGG CCG GAG TAC ACG CCG ATC        552
Pro Lys Ile Ile Gln Thr Arg Arg Pro Glu Tyr Thr Pro Ile
155                 160                 165

CAC CTC AGC TGA                                                564
His Leu Ser  *
    170

ACTGGCACGC GACGAGGACG CATTCCAAAT CATACT                        600

CACGGGAGGA ATCTTTTACT GTGGAGGTGG CTGGTCACGA CTTCTTCGGA          650

GGTGGCAGCC GAGATCGGGG TGCAGAAAT  CCCAGTTCAT GTTGCTCAGA          700

AGAGAATCAA GGCCGTGTCC CCTTGTTCTA ATGCTGCACA CCAGTTACTG          750

TTCATGGCAC CCGGGAATGA CTTGGGCCAA TCACTGAGCT TGTGGTGATC          800

GCACAAGGAC ATTTGGGACT GTCTTGAGAA ACAGATAAT  GATAGTGTTT          850

TGTACTTGTT CTTTCTGGT  AGGTTCTGTC TGTGCCAAGG GCAGGTTGAT          900

CAGTGAGCTC AGGAGAGAGC TTCCTGTTTC TAAGTGGCCT GCAGGGGCCA          950

CTCTCTACTG GTAGGAAGAG GTACACCAGG AAGCCGCCTA GTGCAGAGAG         1000

GTTGTGAAAA CAGCAGCAAT GCAATGTGGA AACTGTAGCG TTTCCTTTCT         1050

CCCCTCATGT TCTCATGTTT GTGCATGTAT ATTACTGATT TACAAGACTA         1100

ACCTTTGTTC GTATATAAAG TTACACCGTT GTTGTTTTAC ATCTTTTGGG         1150

AAGCCAGGAA AGCGTTTGGA AAACGTATCA CCTTTCCCAG ATTCTCGGAT         1200

TCTCGACTCT TTGCAACAGC ACTTGCTTGC GGAACTCTTC CTGGAATGCA         1250

TTCACTCAGC ATCCCCAACC GTGCAACGTG TAACTTGRGC TTTTGCAAAA         1300

GAAGTTGATC TGAAATTCCT CTGTAGAATT TAGCTTATAC AATTCAGAGA         1350

ATAGCAGTTT TAGTGCCAAC TTTTAGTGGG TGAGAAATTT TAGTTTAGGT         1400

GTTTGGGATC GGACCTCAGT TTCTGTTGTT TCTTTTATGT GGTGGTTTCT         1450

ATACATGAAT CATAGCCAAA AACTTTTTCG GAAACTGTTG GTTGAGATAG         1500

TTGGTTCTTT TACCCCACGA AGACATCAAG ATACACTTGT AAATAAAGCT         1550

GATAGCATAT ATTCATACCT GTTGTACACT TGGGTGAAAA GTATGGCAGT         1600

GGGAGACTAA GATGTATTAA CCTACCTGTG AATCATATGT TGTAGGAAAA         1650

GCTGTTCCCA TGTCTAACAG GACTTGAATT CAAAGCATGT CAAGTGGATA         1700

GTAGATCTGT GGCGATATGA GAGGGATGCA GTGCCTTTCC GCATTCATTC         1750

CTGATGGAAT TGTTATACTA GGTTAACATT TGTAATTTTT TTCTAGTTGT         1800

AATGTGTATG TCTGGTAAAT AGGTATTATA TTTTGGCCTT ACAATACCGT         1850

AACAATGTTT GTCATTTTGA AATACTTAAT GCCAAGTAAC AATGCATGCT         1900

TTGAAAATTT GGAACATGGT TTTATTCTTT GAGAAGCAAA TATGTTTGCA         1950

TTAAATGCTT TGATTGTTCG TATCAAGAAA TTGATTGAAC GTTCTCAAAC         2000

CCTGTTTACG GTACTTGGTA AGAGGGAGCC GGTTTGGGAG AGACCATTGC         2050

ATCGCTCNGN CAAGTGTTTC TTGTTAAGTT CCTTTAAACT GGAGAGGCTA         2100

ACCTCAAAAT ACTTTTTTTA CCTGCATTCT ATAATAAATG GGCACAGTAT         2150

GCTCCTTACA AAAAAAAAA  AAAA                                    2174
```

(2) INFORMATION FOR SEQ ID NO: 2:

(i) SEQUENCE CHARACTERISTICS:
  (A) LENGTH: 171 amino acids
  (B) TYPE: amino acid
  (C) STRANDEDNESS: unknown
  (D) TOPOLOGY: unknown  (ii) MOLECULE TYPE: peptide  (xi) SEQUENCE DESCRIPTION: SEQ ID NO: 2:

```
Met Val Tyr Ala Lys Phe Glu Ser Leu Phe Arg Thr Tyr Asp Arg Asp
1               5                   10                  15
Ile Thr Phe Gln Tyr Phe Lys Ser Phe Lys Arg Val Arg Ile Asn Phe
                20                  25                  30
Ser Asn Pro Phe Ser Ala Ala Asp Ala Arg Leu Gln Leu His Lys Thr
            35              40                  45
Glu Phe Leu Gly Lys Glu Met Lys Leu Tyr Phe Ala Gln Thr Leu His
        50              55              60
Ile Gly Ser Ser His Leu Ala Pro Pro Asn Pro Asp Lys Gln Phe Leu
65              70              75                          80
Ile Ser Pro Pro Ala Ser Pro Pro Val Gly Tyr Lys Gln Val Glu Asp
                85              90                      95
Ala Thr Pro Val Ile Asn Tyr Asp Leu Leu Tyr Ala Ile Ser Lys Leu
            100             105                     110
Gly Pro Gly Glu Lys Tyr Glu Leu His Ala Ala Thr Asp Thr Thr Pro
            115                 120             125
Ser Val Val His Val Cys Glu Ser Asp Gln Glu Lys Glu Glu Glu
    130             135                     140
Glu Glu Met Glu Arg Met Arg Arg Pro Lys Pro Lys Ile Ile Gln Thr
145             150                     155                 160
Arg Arg Pro Glu Tyr Thr Pro Ile His Leu Ser
                165                 170
```

(2) INFORMATION FOR SEQ ID NO: 3:

(i) SEQUENCE CHARACTERISTICS:
  (A) LENGTH: 19 base pairs
  (B) TYPE: nucleic acid
  (C) STRANDEDNESS: single
  (D) TOPOLOGY: unknown  (ii) MOLECULE TYPE: DNA (genomic)

(xi) SEQUENCE DESCRIPTION: SEQ ID NO: 3:

CGCGCGGCCG CACWYACCW   19

(2) INFORMATION FOR SEQ ID NO: 4:

(i) SEQUENCE CHARACTERISTICS:
  (A) LENGTH: 17 base pairs
  (B) TYPE: nucleic acid
  (C) STRANDEDNESS: single
  (D) TOPOLOGY: unknown  (ii) MOLECULE TYPE: DNA (genomic)

(xi) SEQUENCE DESCRIPTION: SEQ ID NO: 4:

CGCCCGCGGT CNCAGGT   17

(2) INFORMATION FOR SEQ ID NO: 5:

(i) SEQUENCE CHARACTERISTICS:
  (A) LENGTH: 30 base pairs (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 5:

CGCGTCGACC ACTGCACTCC AGCCTGGGCG                                                         30

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 6:

CGCGTCGACG GGATTACAGG CGTGAGCCAC                                                         30

(2) INFORMATION FOR SEQ ID NO: 7:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 7:

AGGACGTATG ACAAGGACAT C                                                                  21

(2) INFORMATION FOR SEQ ID NO: 8:

(i) SEQUENCE CHARACTERISTICS:
            (A) LENGTH: 25 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 8:

TGAGCAAAAT ATAACTTCAT TTCCT                                                              25

(2) INFORMATION FOR SEQ ID NO: 9:

(i) SEQUENCE CHARACTERISTICS:
            (A) LENGTH: 40 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO: 9:

GAAAGGTGAT GTCCTTGTCA TACGTCCTAA AGAGGGACTC                                              40

(2) INFORMATION FOR SEQ ID NO: 10:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: DNA (genomic)

-continued (x i) SEQUENCE DESCRIPTION: SEQ ID NO: 10:

TGGGATGGAA ACAAGTGGAA                                                           20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown     (i i) MOLECULE TYPE: DNA (genomic)

(x i) SEQUENCE DESCRIPTION: SEQ ID NO: 11:

GTTTTCTCAA GACAGTCCCA A                                                         21

(2) INFORMATION FOR SEQ ID NO: 12:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown     (i i) MOLECULE TYPE: DNA (genomic)

(x i) SEQUENCE DESCRIPTION: SEQ ID NO: 12:

ATCAGTAATA TACATGCACA AA                                                        22